(12) United States Patent
Laufer (10) Patent No.: US 6,506,196 B1
(45) Date of Patent: Jan. 14, 2003

(54) DEVICE AND METHOD FOR CORRECTION OF A PAINFUL BODY DEFECT

(75) Inventor: Michael D. Laufer, Menlo Park, CA (US)

(73) Assignee: NDO Surgical, Inc., Mansfield, IL (US)

( * ) Notice: Subject to any disclaimer, the term of this patent is extended or adjusted under 35 U.S.C. 154(b) by 0 days.

(21) Appl. No.: 09/519,945

(22) Filed: Mar. 7, 2000

Related U.S. Application Data (60) Provisional application No. 60/140,492, filed on Jun. 22, 1999.

(51) Int. Cl.[7] .............................................. A61B 17/10
(52) U.S. Cl. ..................... 606/142; 600/141; 227/175.1
(58) Field of Search .................................. 606/151, 153, 606/156, 219, 220, 221, 142, 143, 139; 623/23.65, 23.67; 600/207, 139, 140, 146; 227/175.1, 175.3, 175.8; 128/898; 604/26

(56) References Cited

U.S. PATENT DOCUMENTS

| | | | | |
|---|---|---|---|---|
| 3,551,987 A | * | 1/1971 | Wilkinson | 227/178.1 |
| 5,088,979 A | * | 2/1992 | Filipi et al. | 604/26 |
| 5,433,721 A | * | 7/1995 | Hooven et al. | 606/143 |
| 5,465,894 A | * | 11/1995 | Clark et al. | 227/175.1 |
| 5,571,116 A | * | 11/1996 | Bolanos et al. | 227/178.1 |
| 5,787,897 A | * | 8/1998 | Kieturakis | 128/898 |
| 6,086,600 A | * | 7/2000 | Kortenbach | 606/220 |
| 6,159,146 A | * | 12/2000 | El Gazayerli | 600/106 |

* cited by examiner

Primary Examiner—David O. Reip
Assistant Examiner—Julian W. Woo
(74) Attorney, Agent, or Firm—Burns, Doane, Swecker & Mathis LLP (57) ABSTRACT

According to one aspect of the invention, a device for performing a medical procedure includes a first elongated member that is adapted to be positioned inside of an esophagus and a stomach, the first elongated member having a distal flexible portion having a first retracted configuration and a second expanded configuration, the second expanded configuration defining an arcuate shape. The device also includes a second elongated member that is located adjacent to the first elongated member and is adapted to be positioned inside of the esophagus and the stomach, the second elongated member having a proximal flexible portion and a distal flexible portion, the proximal flexible portion having a first expanded configuration and a second expanded configuration, the second expanded configuration defining an arcuate shape, the distal flexible portion having a first retracted configuration and a second expanded configuration defining an arcuate shape, the proximal flexible portion and the distal flexible portion being coaxially aligned with each other when in the first retracted configuration.

22 Claims, 8 Drawing Sheets

DEVICE AND METHOD FOR CORRECTION OF A PAINFUL BODY DEFECT

RELATED APPLICATIONS

This application is based on U.S. Provisional Patent Application Ser. No. 60/140,492 entitled "Stomach Elevator Method and Device," filed on Jun. 22, 1999.

BACKGROUND OF THE INVENTION

1. Field of the Invention

The invention relates to a treatment system and device for treating gastro-esophageal reflux, and more particularly, the invention relates to a minimally invasive method and device for performing fundoplication.

2. Brief Description of the Related Art

A common condition that affects many people is heartburn. This condition occurs in as much as half of the U.S. population. Daily heartburn may occur in as many as 10 percent of U.S. population. Heartburn is caused by stomach acid reflux which causes stomach acid to enter the esophagus resulting in pain and discomfort. Prolonged contact of the esophagus to stomach acid results in a condition known as Barrett's esophagus. This condition can be pre-cancerous.

Gastro-esophageal reflux disease (G.E.R.D.) is thought to be due to a condition where the lower esophageal sphincter becomes loose over time because of stretching and ageing. This lower esophageal sphincter is formed by the hiatus were the esophagus passes through the diaphragm. As the diaphragm becomes loose, the ability of the diaphragm to put adequate pressure on the esophagus to close it and prevent stomach acid from passing back up past the diaphragm becomes diminished. If the esophagus cannot be adequately compressed, acid is allowed to reflux into the esophagus from the stomach. This is especially true when the patient is supine, has a full stomach, or both.

Currently there are two established solutions for this problem. The first and most commonly used solution is to prescribe medications to either neutralize the acid or to eliminate its production altogether. These medications can be quite expensive, costing between about one thousand and three thousand dollars per year. There also is some controversy whether these medications prevent the cancerous condition in the esophagus. The other alternative is to have surgery. The surgery generally consists of wrapping the stomach or part of the stomach around the esophagus and fixing it in place. The surgery can be accomplished either through a large incision made in the abdomen or through minimally invasive surgery using a laparoscope. Both kinds of surgery require a general anesthetic and usually take between four and eight hours to accomplish. In addition, laparoscopic surgery requires a great deal of surgical skill.

From an economic perspective, surgical treatment requires that a specific physician, usually a gastroenterologist, diagnose the patient and then refer the patient to another physician, usually a general surgeon, for the corrective procedure at a later date. Because the gastroenterologist cannot perform the surgery himself, there is a natural tendency for the gastroenterologist to simply prescribe medication for the patient rather than recommending surgery. Because the patient must take the medication daily, there are a large number of patients who are unsatisfied with this treatment regimen. If a simplified curative surgical procedure were available, which the gastroenterologist could perform in his office at the time that the diagnosis is made, patients would generally opt for the procedure.

Therefore, there is a need for devices and methods for their use, which would allow the gastroenterologist to perform the fundoplication procedure to eliminate gastric acid reflux into the esophagus.

The surgical procedure currently performed for these conditions is commonly referred to as the Nissen fundoplication. This procedure entails the placement of approximately 5 surgical insertion ports into the patient at various locations throughout the abdomen. Instruments are inserted and removed through the ports while visualizing the tips of the instruments inside the patient by means of a camera inserted through one of the ports. The instruments are used to cut and mobilize tissue from around the stomach so that it may be twisted around the esophagus. The stomach is wrapped around the esophagus and is then sutured in place at approximately one end of the stomach, such that a cuff is formed around the lower esophagus. This cuff of stomach around the esophagus may serve as a spacer so that the lower esophagus may be closed by the diaphragmatic muscles through which the lower esophagus passes. Alternatively, it may help to twist the stomach into the shape of a sphincter to close the opening back into the esophagus.

This type of surgery is usually very successful. One complication that may occur, however, includes the inability to swallow because the cuff is too tight around the esophagus. Another common complication is the inability to belch, or relieve gas and pressure from the stomach. Finally, when a long period of time has passed after the surgery, the cuff may slowly slip off the bottom of the lower esophagus, which allows acid to reflux into the esophagus again.

Two recent innovations allow for the stomach to be invaginated into the esophagus. According to one method an instrument is placed into the esophagus and expanded into the stomach and the stomach is perforated with the instrument. The stomach is then pulled into the esophagus. This allegedly creates an artificial valve in the esophagus. In one recently issued patent, U.S. Pat. No. 5,787,897, a device is inserted through the esophagus and into the stomach. This device as shown in the patent can be flexed and rotated to allow manipulation of the stomach around the esophagus. As shown in the patent, laparoscopic abdominal access is required in order to accomplish this procedure. As the stomach is held in place with the instrument inserted through the esophagus, laparoscopic surgical procedures are used to suture the stomach in place. This procedure still requires that the patient be under general anesthesia.

It would be desirable to provide a simplified method for the fundoplication procedure that can be performed by the gastroenterologist entirely through the esophagus without the need for general anesthesia.

SUMMARY OF THE INVENTION

The present invention relates to a device and method for performing fundoplication in which the treatment is performed entirely through the esophagus of the patient without making incisions into the abdomen or stomach.

According to one aspect of the invention, a device for performing fundoplication includes a first elongated member that is adapted to be positioned inside of an esophagus and a stomach, the first elongated member having a distal flexible portion having a first retracted configuration and a second expanded configuration, the second expanded configuration defining an arcuate shape. The device also includes a second elongated member that is located adjacent to the first elongated member and is adapted to be positioned inside of the esophagus and the stomach, the second elongated member having a proximal flexible portion and a distal flexible portion, the proximal flexible portion having a first expanded configuration and a second expanded configuration, the second expanded configuration defining an arcuate shape, the distal flexible portion having a first retracted configuration and a second expanded configuration defining an arcuate shape, the proximal flexible portion and the distal flexible portion being coaxially aligned with each other when in the first retracted configuration.

Another aspect of the present invention discloses a method of performing a fundoplication procedure, including the steps of contacting a fundus portion of the stomach with an elongate member and moving the fundus portion of the stomach around the esophagus. After the fundus portion of the stomach is moved around the esophagus, the fundus portion is fastened to a different portion of the stomach.

The present invention does not require perforation of the stomach in order to manipulate it into position. This innovation is important because the contents of the stomach, if allowed to leak into the abdominal cavity, could cause severe harm to the patient. The present invention also differs substantially from all other procedures known in the prior art because it does not require laparoscopic access to the abdomen and, due to it's simplicity, does not require internal transabdominal visualization or general anesthesia.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

Figure 1:
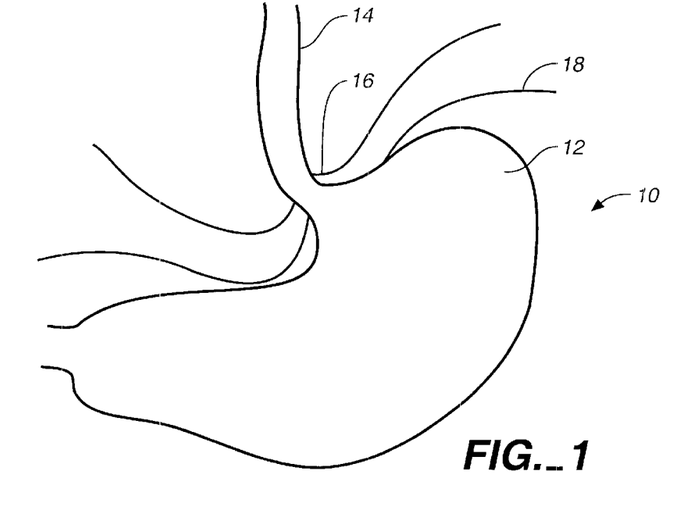
FIG. 1 is a side elevational view of a stomach and an esophagus.

According to the present invention, a fundoplication procedure, or method, includes relocating and fastening a first portion of the stomach to a second portion of the stomach. As shown in FIG. 1, a stomach 10 includes a fundus 12 with an esophagus 14 defining the passageway into the stomach 10. A junction between the stomach 10 and the esophagus 14 is a gastro-esophageal (GE) junction 16. The diaphragm 18 is muscular tissue that helps to open and close the GE junction 16.

Figure 2:
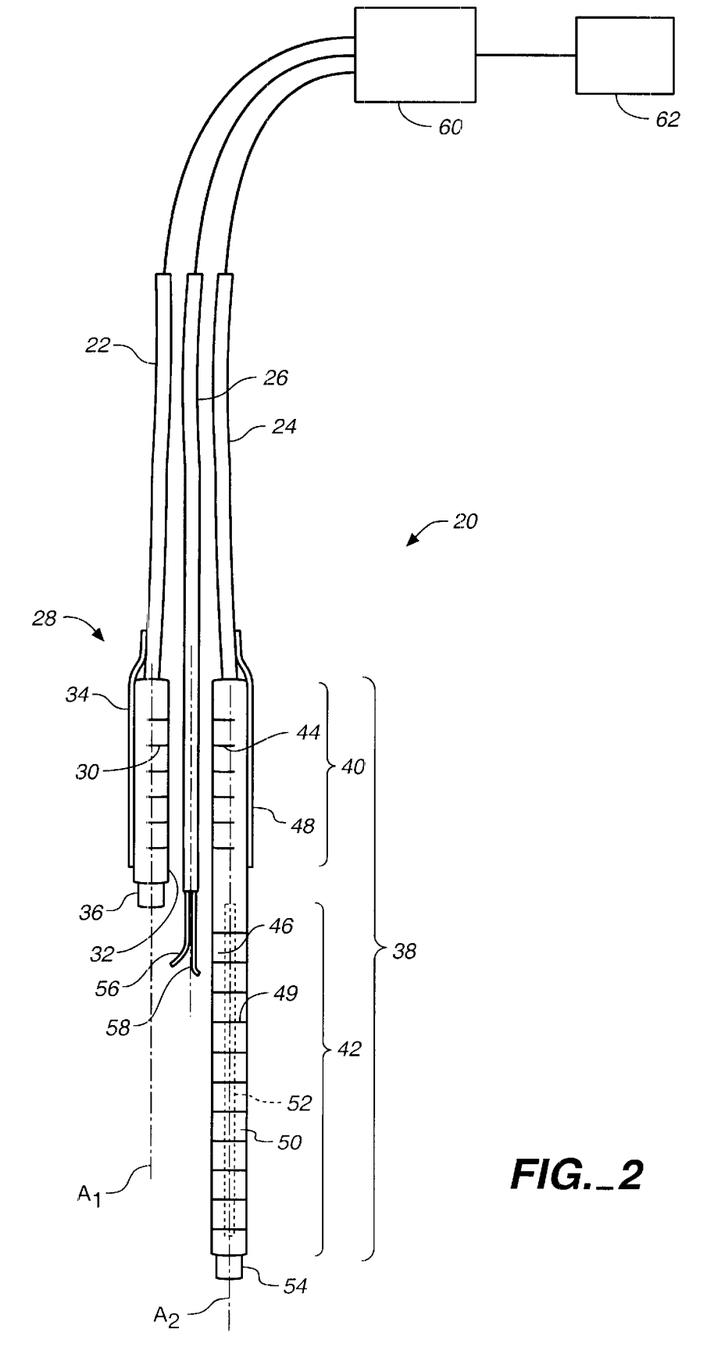
FIG. 2 is a front elevational view of a device according to the present invention.
Figure 4:
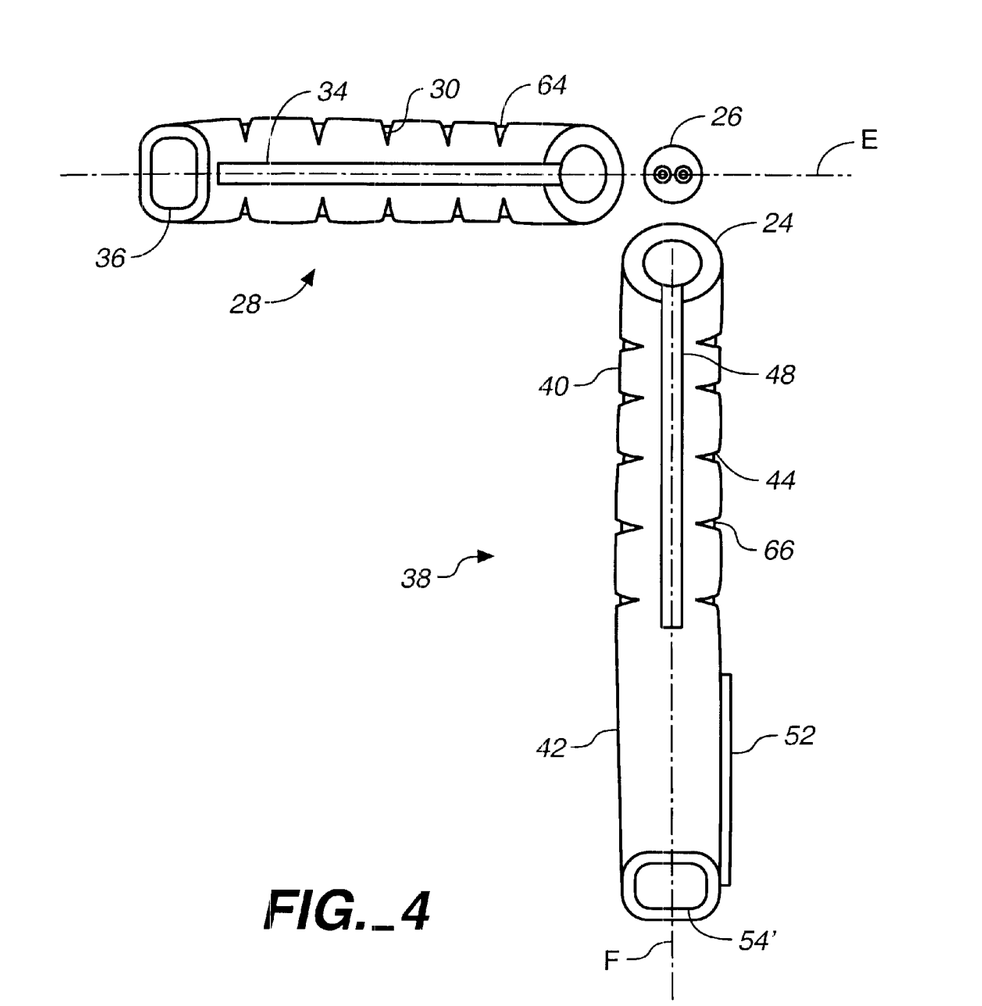
FIG. 4 is a top view of the device according to the present invention as shown in FIG. 3, showing a first elongated portion and a second elongated portion in expanded positions.
Figure 5:
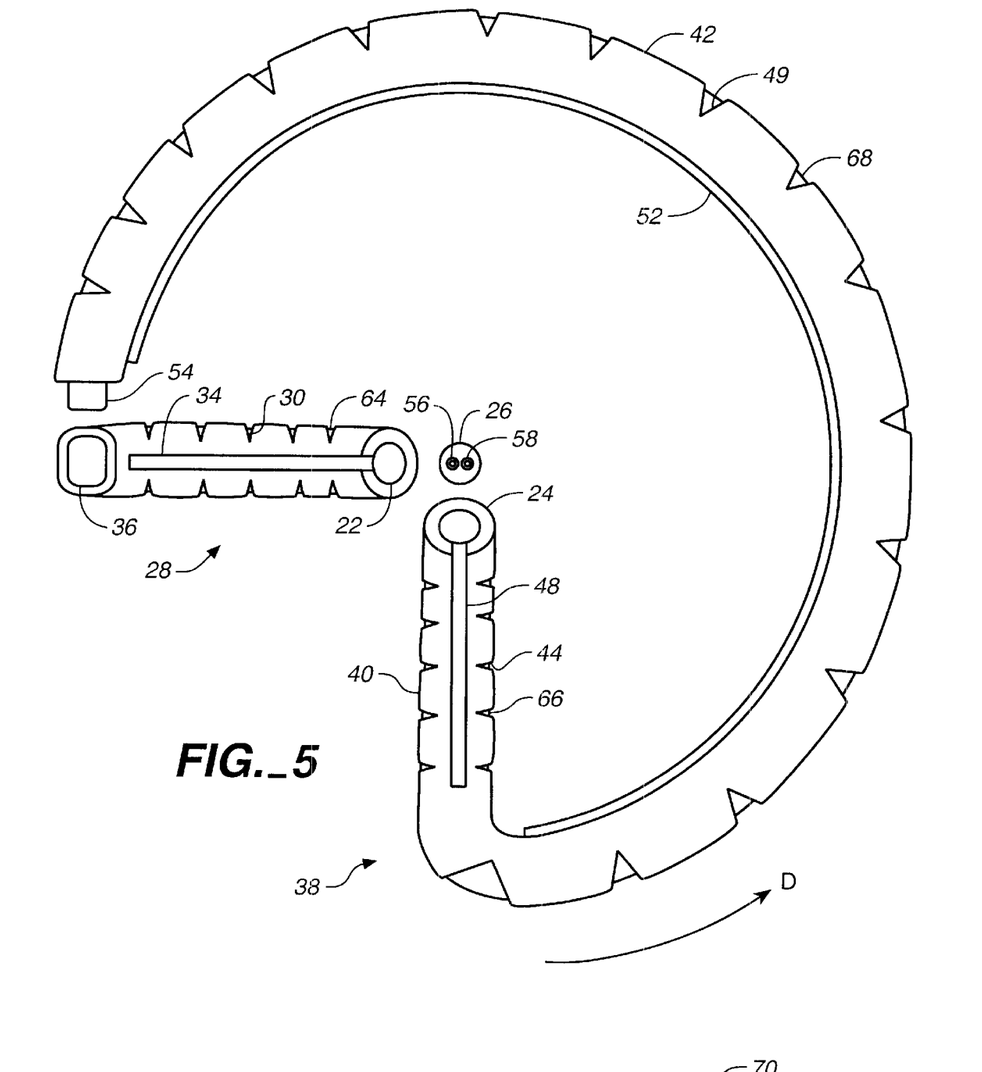
FIG. 5 is a top view of the device according to the present invention, showing a first elongated portion and a second elongated portion in expanded positions, with a flexible distal end of the second elongated portion also in an expanded position.

A device 20 for performing the fundoplication procedure according to the present invention is shown in FIG. 2 and includes a first elongated member 22, an adjacently located second elongated member 24, and a third elongated member 26. The three elongated members 22, 24 and 26 are positioned side by side and are of different lengths. The first elongated member 22 is shorter in length than the second and the third elongated members 24 and 26. Preferably the elongated members 22, 24 and 26 are connected at their proximal ends, or alternatively, along a substantial portion of their lengths. The first and second elongated members 22 and 24 are constructed in such a way that the distal portions of each member are bendable. The first elongated member 22, as shown in FIGS. 4 and 5, is bendable along Plane E. The second elongated member 24 is bendable in a first Plane F and then in a second plane (not shown) that is orthogonal to Plane F. As further described below, the first and second elongated members 22 and 24 are bendable from a remote location outside the patient's body to allow for the manipulation of a hollow organ, such as a stomach, in a desired fashion.

The first elongated member 22 includes a proximal portion and an opposite distal portion. The distal portion includes a flexible portion 28. A plurality of axially aligned slits 30 extend generally perpendicular to longitudinal axis $A_1$ approximately the length of the flexible portion 28 along an inner side 32. Located opposite of the slits 30 is a stiffening rib 34, which makes the stiffening rib side of the flexible portion 28 stiffer than the inner side 32 with the slits 30. At a termination point of the flexible portion 28 is an optional anvil 36, which will be explained in further detail below. The first elongated member 22, including the proximal and distal portions, extend along the longitudinal axis $A_1$ when in the retracted position.

The second elongated member 24 includes a proximal portion and an opposite distal portion. The distal portion includes a multi-flexible portion 38, which includes a proximal flexible portion 40 and an adjacent distal flexible portion 42. The proximal flexible portion 40 is bendable in only a first Plane F and the distal flexible portion 42 is only bendable in a second plane that is orthogonal to plane F. The distal flexible portion 42 includes a plurality of axially aligned slits 44 that extend generally perpendicular to longitudinal axis $A_2$ approximately the length of the proximal flexible portion 40 along an inner side 46. Located opposite of the slits 44 on the proximal flexible portion 40 is a stiffening rib 48, which makes the stiffening rib side of the flexible portion stiffer than the inner side 46 with the slits 44. As shown in FIG. 2, the second elongated member 24, including the proximal and distal portions, extend along longitudinal axis $A_2$ when in the retracted position. The distal flexible portion 42 is coaxially aligned with the proximal flexible portion 40 and longitudinal axis $A_2$ when the second elongated member 22 is in a retracted or relaxed position. The distal flexible portion 42 includes a plurality of axially aligned slits 49 along an outer side 50 that is located approximately 90 degrees from the inner side 46. At a termination point of the distal flexible portion 42 is a stapler 54, which will be explained in further detail below. Located opposite of the slits 49 on the distal flexible portion 42 is a stiffening rib 52. The slit side of the flexible portions are more flexible than the stiffening rib side of the flexible portions. The slits allow for the expansion of the sides opposite the stiffening ribs when internal bladders are inflated or expanded as further described below. The stiffening ribs provide stiffness along a side of the flexible portions so that when internal bladders are inflated or expanded, the flexible portions provide stiffness in the required plane.

The third elongated member 26 has a plurality of channels for accommodating a variety of scopes. The scopes may be included with the device 20 or may be separately purchased and inserted into the channels for use with the device. In one example, the third elongated member 26 includes a first utility scope 56 and a second utility scope 58, which may be used for visualization and as a light source. Additional utility tubes or scopes may be incorporated into the third elongated member 26 as needed. For example, a suction tube or a medication delivery tube may be incorporated into the third elongated member 26. The third elongated member 26 is not necessary to perform the fundoplication as described herein and, therefore, is optional.

The device 20 according to the present invention includes a controller 60 and a pneumatic or hydraulic source 62. The controller 60 is manually operated by the physician. In the alternative, the controller 60 includes a programmable interface that may include either a micro-processor that is integral with the device 20 or a personal computer communicating with the device 20, which includes a manual override for the physician.

Figure 3:
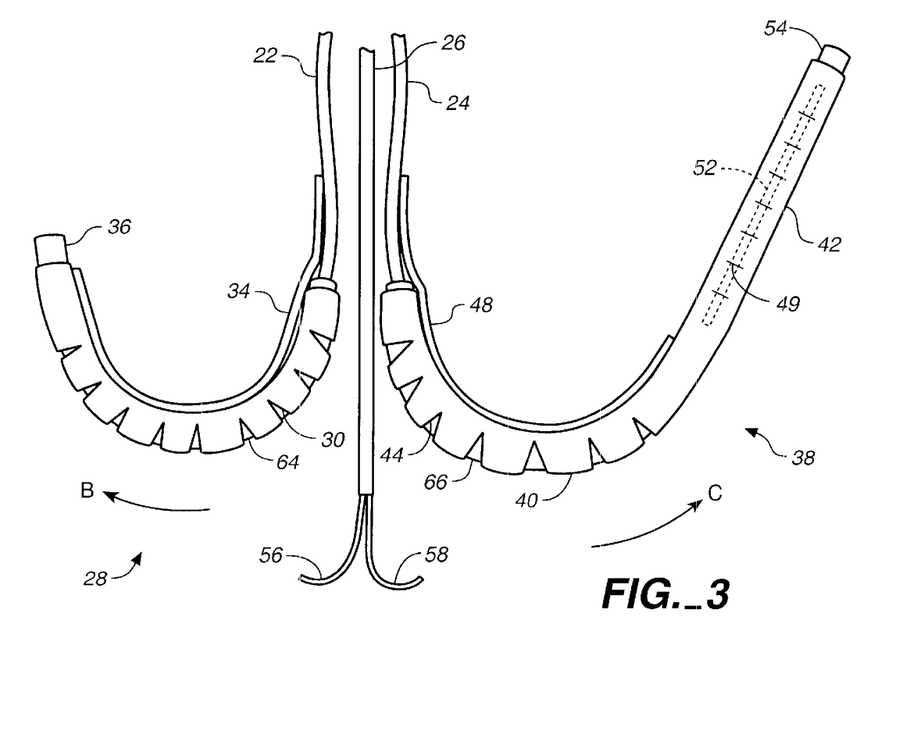
FIG. 3 is a front plan view of the device according to the present invention, showing a first elongated member and a second elongated member in expanded positions.

As shown in FIGS. 3–5, the first and second elongated members 22 and 24 each have a first or relaxed configuration and a second or expanded configuration. The first elongated member 22 has a bladder 64 located internal of the flexible portion 28. The second elongated member 24 has a proximal bladder 66 located internal of the proximal flexible portion 40 and a distal bladder 68 located internal of the distal flexible portion 42. As shown in FIGS. 3 and 4, the bladder 64 is inflated, or expanded, with compressed gas or fluid via a conduit in the elongated member to expand the bladder 64, causing the weaker side with the slits 30 to bend more than the relatively rigid side with the stiffening rib 34. The flexible portion 28 moves in the direction B to define the expanded configuration, which is arcuate in shape forming an angle of about 150 degrees. Likewise, the proximal bladder 66 is inflated with compressed gas or fluid through a conduit to cause the proximal flexible portion 40 to move in the direction C to define the expanded configuration, which also is arcuate in shape to mirror the flexible portion 28 forming an angle of about 150 degrees relative to the proximal end. As shown in FIG. 5, the distal bladder 68 is inflated with compressed gas or fluid through a conduit to likewise cause the distal flexible portion 42 to move in the direction D to define the expanded configuration, which is also arcuate in shape forming an angle of about 90 to 360 degrees. The flexible portion 28 is expanded on a first plane and the proximal flexible portion 40 is expanded on a second plane that is approximately 90 degrees, or perpendicular, to the first plane. The distal flexible portion 42 is expanded on a third plane that is approximately 90 degrees, or perpendicular, to the first and the second planes. When the portions are fully expanded, the terminating point or stapler 54 of the distal flexible portion 42 is adjacent to and aligned with the terminating point or anvil 36 of the flexible portion 28.

Figure 6:
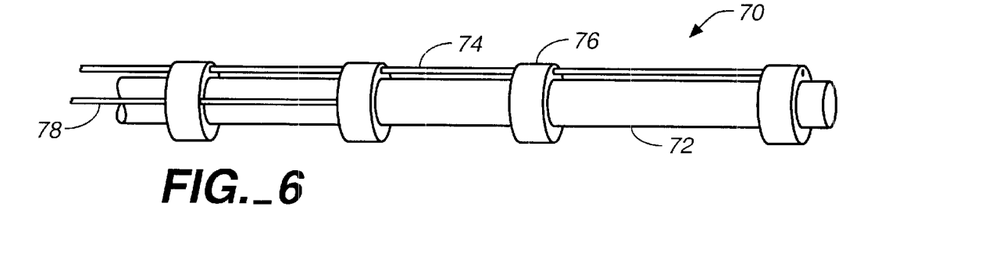
FIG. 6 is a perspective view of an alternative embodiment of a second elongated portion according to the present invention.

The elongated member flexible portions may be achieved in a variety of different ways. One alternative elongated member 70 is shown in FIG. 6, which includes a flexible portion 72, which is flexible in one dimension and is rigid in another dimension. The flexible portion 72 is provided with a pull fiber 74 and a plurality of collars 76. The pull fiber 74 extends through the collars to a proximal end of the flexible portion 72. When the pull fiber 74 is actuated from the exterior of the patient's body the flexible portion 72 is bent to a predetermined configuration. For the longer member, or second elongated member used in the device 20, the elongated member 70 has a proximal flexible portion and a distal flexible portion. The first pull fiber 74 is provided to bend the proximal flexible portion of the flexible portion 72 into the second configuration or arcuate shape and a second pull fiber 78 is provided to bend the distal flexible portion to the second configuration. Although a pull fiber is described, it should be understood that a pull string, or other means, may be easily substituted for the pull fiber to actuate the flexible portions.

Figure 7:
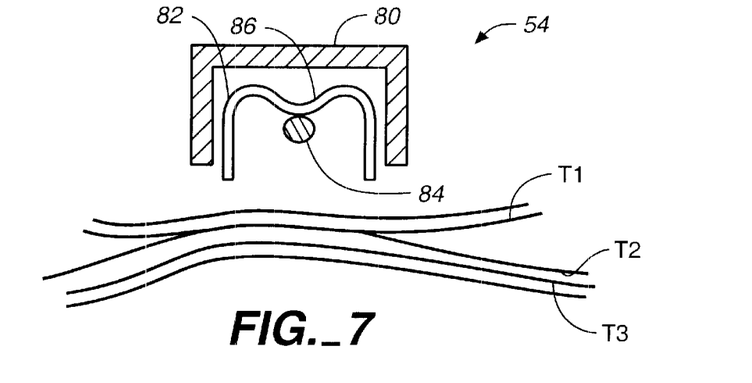
FIG. 7 is a side cross sectional view of a one sided stapler shown adjacent to stomach tissue according to the present invention.
Figure 8:
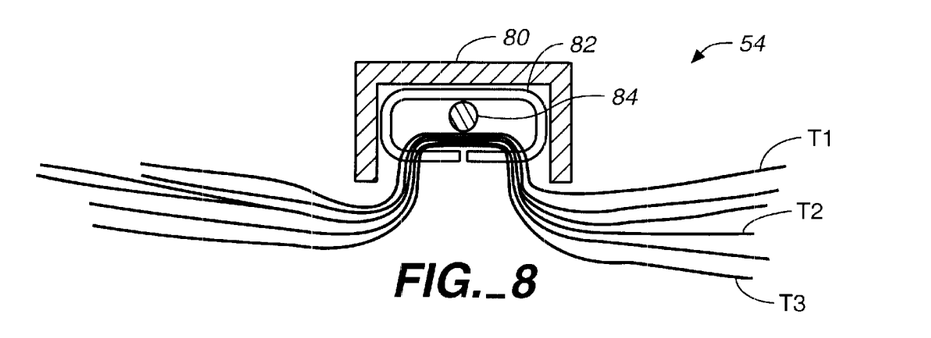
FIG. 8 is a side cross sectional view of the one sided stapler shown stapling stomach tissue together according to the present invention.

In the preferred embodiment shown in FIGS. 7 and 8, the stapler 54 is a self stapling device which does not require an anvil. The stapler 54 is located at the distal end of one of the elongated members 22 or 24 and includes a housing 80 containing a staple 82. The self stapling device also includes a contact bar 84 for contacting an activation surface of the staple. The staple 82 includes an indentation 86 so that the staple ends come together as staple is bent around the contact bar 84. When the stapler housing 80 is moved forward toward the stomach and connective tissue layers, shown as $T_1$, $T_2$ and $T_3$, to staple the tissue layers together, the bar 84 is maintained stationary and the ends of the staple 82 are caused to penetrate the tissue and bend over to secure the tissue layers together. A bladder may be utilized to cause the movement of the stapler housing 80.

Figure 9:
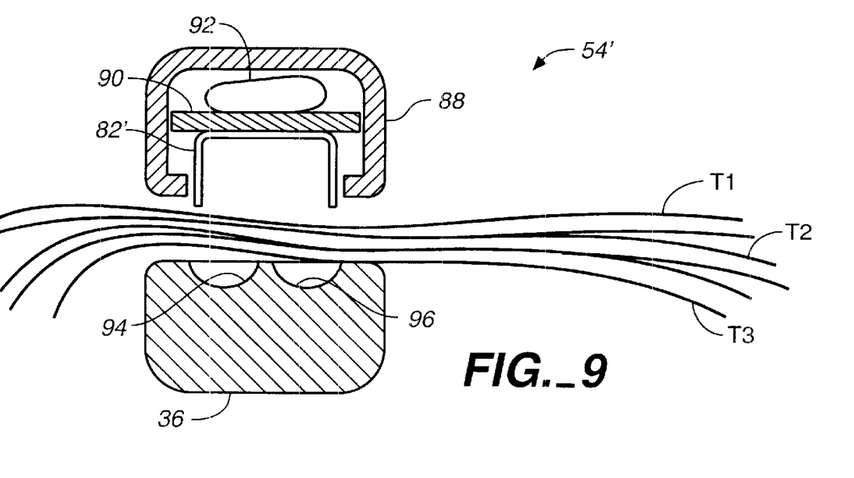
FIG. 9 is a cross sectional view of an alternative embodiment of a stapler and an anvil according to the present invention.

In an alternative embodiment, and as shown in FIGS. 3–5 and 9, one of the elongated members 22 or 24 is provided with the stapler 54' and the other member is provided with the anvil 36. A staple 82' is used to secure a layer of connective tissue T1 outside of the stomach and two layers of tissue T2, T3 outside the stomach together. The stapler 54' includes a housing 88, a movable plate 90, a bladder 92 and the anvil 36. The anvil includes first and second recesses 94 and 96 respectively. Upon inflation of the bladder 92, the movable plate forces the staple 82' forward out of the housing 88. As the staple 82' is moved forward, the ends of the staple penetrate the tissue layers T1, T2, T3 and are bent over by staple receiving recesses 94 and 96 of the anvil 36. The devices of FIGS. 7–8 and 9 are merely two examples of securing mechanisms which may be used with the present invention.

When the elongated members 22, 24 and 26 are inserted through the throat into the esophagus of a patient, the elongated members protrude into the stomach. When the bending mechanism is actuated, the first elongated member 22 bends to hold part of the stomach against the connective tissue surrounding its lesser curvature while the second elongated member 24 bends to reposition the fundus of the stomach around the esophagus. The stapling mechanism provided on one or more of the elongated members 22, 24 is then actuated which accomplishes fastening of the fundus to the part of the stomach held by the short member. The device is not required to be rotated in the esophagus and the stomach is not perforated prior to its being secured in the correct position. Another novel feature of the device and method disclosed is that the arc length of the flexible portion manipulated along the esophagus controls the tightness of the resulting fundoplication procedure.

Figure 10:
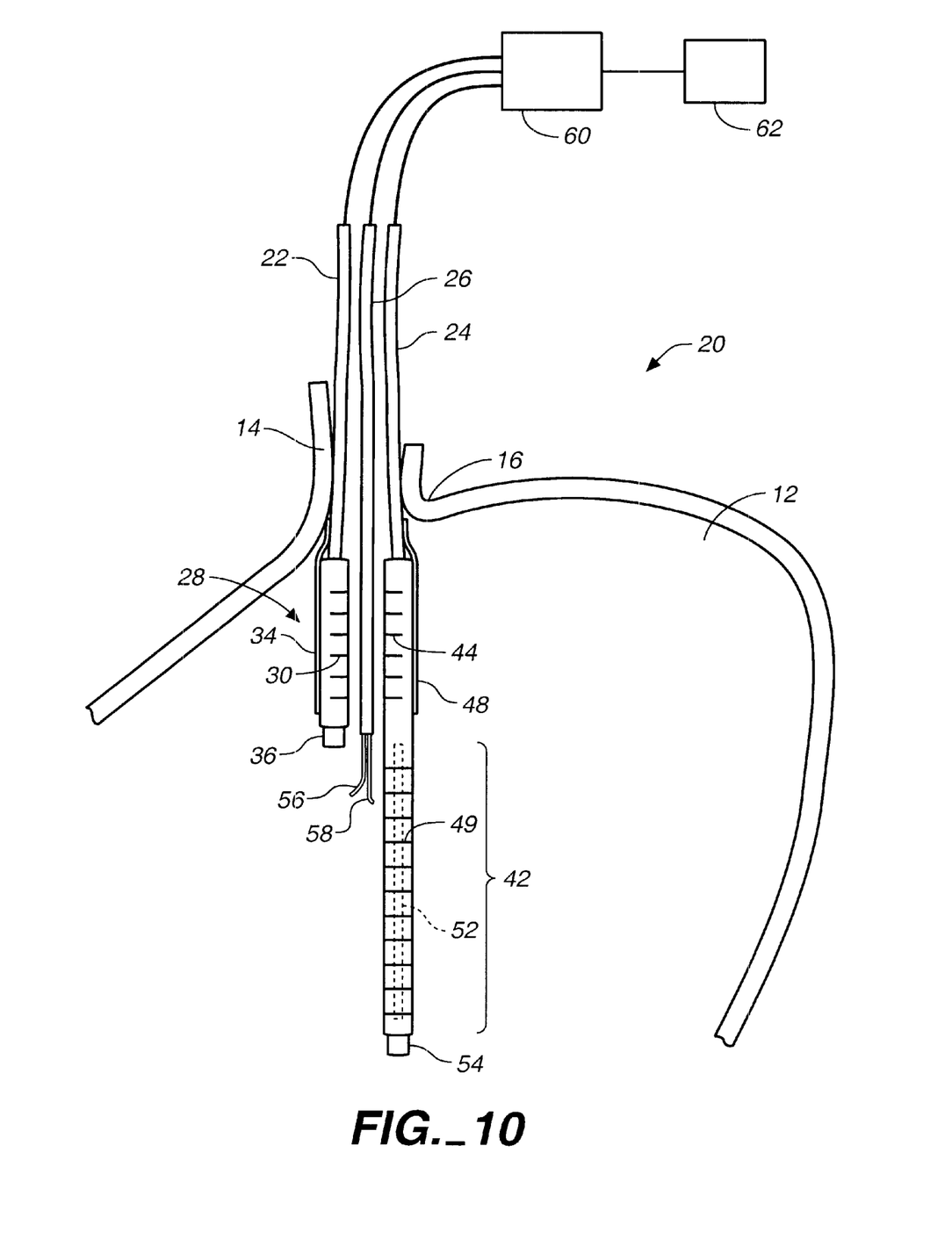
FIG. 10 is a side cross sectional view of a portion of a stomach and an esophagus with the device inserted into the stomach, showing a step of the method according to the present invention.
Figure 11:
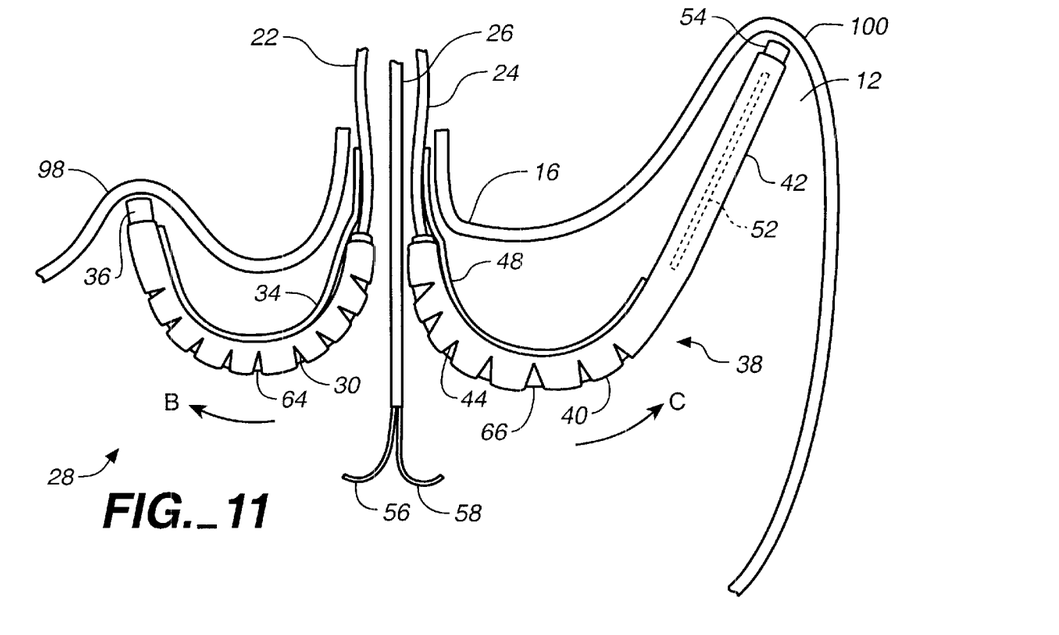
FIG. 11 is a side cross sectional view of the stomach and the esophagus with the device inserted into the stomach, showing an additional step of the method according to the present invention.

Referring to FIG. 10, the device 20 has been inserted through the esophagus 14 of a patient and into the patient's stomach 10. The flexibility of the elongated members 22 and 24 is controlled from their proximal ends external to the patient's body by the controller 60 and the pneumatic or hydraulic source 62. As shown in FIG. 11, in a first step of the method according to the present invention, the first elongated member 22 is bent upwards approximately 90 degrees in the direction of the arrow B to contact and grasp and hold an upper stomach portion 98 securely in place against the connective tissue external to the stomach. Then, the second elongated member 24 is bent upwards in the direction of arrow C by inflating the proximal bladder 66 causing the second elongated distal flexible portion 42 to contact and grasp a fundus portion 100.

Figure 12:
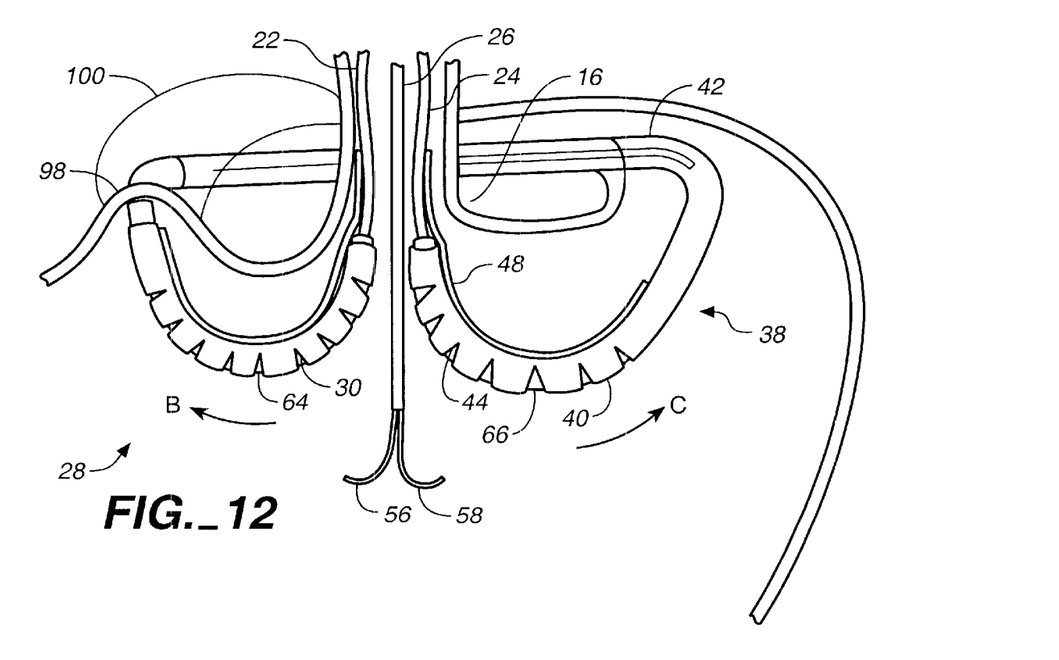
FIG. 12 is a side cross sectional view of the stomach and the esophagus with the device inserted into the stomach, showing another step of the method according to the present invention.
Figure 13:
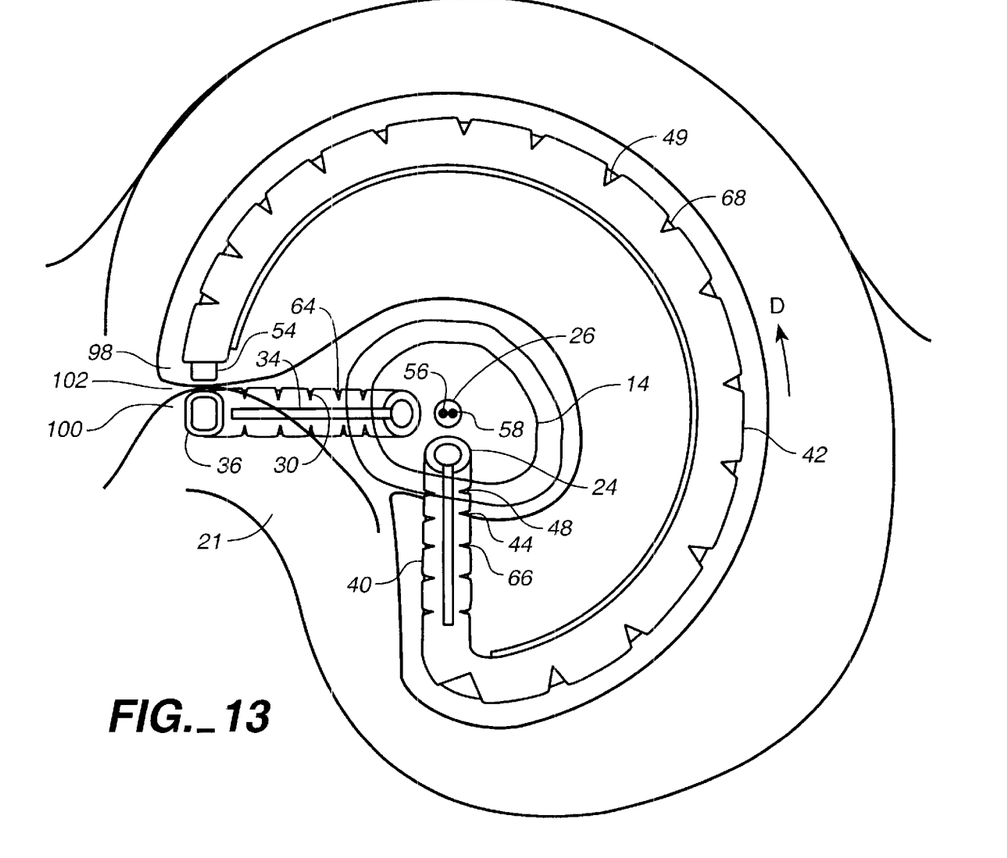
FIG. 13 is a top cross sectional view of the stomach and the esophagus with the device inserted into the stomach, showing the step of FIG. 12.
Figure 14:
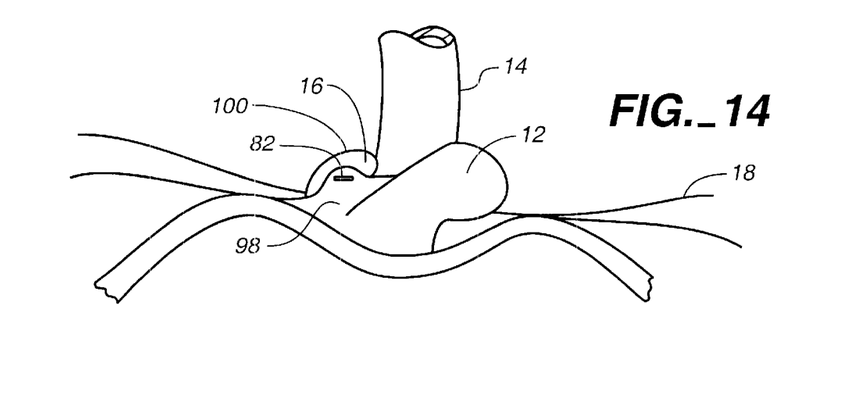
FIG. 14 is a side partial cross sectional view of the stomach showing a final configuration of the stomach after the procedure.

As shown in FIGS. 12–13 and as described above, the second elongated member 24, and particularly the distal flexible portion 42, is bent approximately 90 degrees from the proximal flexible portion 40. After the second elongated member 22 has been bent upwards in a first dimension, the distal flexible portion 42 and the fundus portion of the stomach is bent around the esophagus 14 in the direction of the arrow D, as shown in FIG. 13. This bending of the distal flexible portion 42 repositions the fundus of the stomach around the esophagus as shown in FIGS. 12–14. Once the distal flexible portion 42 has been actuated and the fundus is positioned around the esophagus, the terminating end of the second elongated member distal flexible portion 42 is positioned directly proximate to the terminating end of the first elongated member flexible portion 28 with tissue located in between the two portions. In this position, the two elongated members 22 and 24 are preferably arranged for securing the tissue in place with a securing mechanism, such as the stapler discussed above, provided at the terminating ends of the elongated members 22 and 24. The terminating ends of the elongated members 22 and 24 are positioned on opposite sides of two layers of tissue forming a junction 102 for securing the tissue together with a securing mechanism such as the staple 82 or 82' discussed above. Alternatively, a suture or any other known securing device may be used.

The present invention provides a device and method which can be used by a gastroenterologist rather than a surgeon to reposition and secure the fundus of the stomach about the esophagus to treat gastroesophageal reflux. Because the device is fully automatic and operated from an exterior of the patient's body, no visualization of the procedure is required and thus no laparoscopic ports are required in the abdomen or stomach for the camera. In addition, because the device is operated automatically, the physician does not manually move parts of the stomach which greatly reduces the risk of tearing the fragile stomach or esophagus walls due to excessive force being applied. The pneumatic or hydraulic source 62 together with controller 60 reduce the possibility of tearing by providing a maximum operation pressure and rate of pressure rise at which the device is operated to prevent tearing of tissue.

Since the device of the present device is novel and it is intended to be used in a human, it is important that the physician be instructed to use the device mechanisms and methods disclosed herein. The training of the device and method may be accomplished on a cadaver or a human model, or may be accomplished at the bed side of a patient. Further, as it would be appreciated by those skilled in the art, the device of the present invention should be sterilized before use.

FIG. 14 shows the stomach after the fundoplication procedure showing the stomach portion 98 stapled to the fundus portion 100 with staple 82 at junction 102.

The simplification of the fundoplication procedure with the device of the present invention allows the gastroenterologist to perform the procedure described above without any special expertise in laparoscopic surgery and without having to refer the patient to a surgeon for the procedure. Accordingly, the procedure can be made available to many more patients less expensively.

While the invention has been described in detail with reference to the preferred embodiments thereof, it will be apparent to one skilled in the art that various changes and modifications can be made and equivalents employed, without departing from the present invention.

What is claimed is:

1. A single device for performing a fundoplication procedure, comprising:
   a first elongated member that is adapted to be positioned inside of an esophagus and a stomach, the first elongated member having a distal flexible portion having a first retracted configuration and a second expanded configuration, the second expanded configuration defining an arcuate shape; and
   a second elongated member that is located adjacent to the first elongated member and is adapted to be positioned inside of the esophagus and the stomach, the second elongated member having a proximal flexible portion and a distal flexible portion, the proximal flexible portion having a first expanded configuration and a second expanded configuration, the second expanded configuration defining an arcuate shape, the distal flexible portion having a first retracted configuration and a second expanded configuration defining an arcuate shape, the proximal flexible portion and the distal flexible portion being coaxially aligned with each other when in the first retracted configuration.

2. The device of claim 1, further comprising:
   the first and the second elongated members having a terminating distal end; and
   a fastening device located at one of the terminating distal ends.

3. The device of claim 2, wherein the fastening device is a stapling device.

4. The device of claim 2, wherein the fastening device further comprises:
   a housing containing a staple;
   a contact bar for contacting an activation surface of the staple; and
   an indentation so that the staple ends come together as the staple is bent around the contact bar.

5. The device of claim 1, wherein the second elongated member distal flexible portion is located adjacent to the first elongated member when both portions are in the expanded configurations.

6. The device of claim 5, wherein the second elongated member distal flexible portion is aligned with the first elongated member when both portions are in the expanded configurations.

7. The device of claim 1, further comprising:
a third elongated member that is adapted to be positioned inside of the esophagus and the stomach.

8. The device of claim 1, wherein the second elongated member proximal flexible portion is expanded on a first plane and the second distal elongated member distal flexible portion is expanded on a second plane.

9. The device of claim 8, wherein the first plane is approximately orthogonal to the second plane.

10. The device of claim 1, wherein the arcuate shape further includes an arcuate length, which controls the tightness of the resulting fundoplication procedure.

11. The device of claim 1, wherein the device is sterilized.

12. A device for performing a fundoplication procedure, comprising:
a first elongated member that is adapted to be positioned inside of an esophagus and a stomach, the first elongated member having a distal flexible portion having a first retracted configuration and a second expanded configuration, the second expanded configuration defining an arcuate shape;
a second elongated member that is located adjacent to the first elongated member and is adapted to be positioned inside of the esophagus and the stomach, the second elongated member having a proximal flexible portion and a distal flexible portion, the proximal flexible portion having a first expanded configuration and a second expanded configuration, the second expanded configuration defining an arcuate shape, the distal flexible portion having a first retracted configuration and a second expanded configuration defining an arcuate shape, the proximal flexible portion and the distal flexible portion being coaxially aligned with each other when in the first retracted configuration, wherein
the elongated members each having a flexible portion with an internal bladder, a stiffening rib located on the elongated member that extends longitudinally along the length of the elongated members, and a plurality of slits located on the opposite side of the stiffening rib.

13. The device of claim 12, wherein the flexible portion side with the stiffening rib is stiffer than the side with the plurality of slits.

14. A device for performing a fundoplication procedure, comprising:
a first elongated member that is adapted to be positioned inside of an esophagus and a stomach, the first elongated member having a distal flexible portion having a first retracted configuration and a second expanded configuration, the second expanded configuration defining an arcuate shape;
a second elongated member that is located adjacent to the first elongated member and is adapted to be positioned inside of the esophagus and the stomach, the second elongated member having a proximal flexible portion and a distal flexible portion, the proximal flexible portion having a first expanded configuration and a second expanded configuration, the second expanded configuration defining an arcuate shape, the distal flexible portion having a first retracted configuration and a second expanded configuration defining an arcuate shape, the proximal flexible portion and the distal flexible portion being coaxially aligned with each other when in the first retracted configuration, wherein the first and the second elongated members having a terminating distal end; and
a fastening device located at one of the terminating distal ends, wherein the fastening device further comprises:
a housing for containing a staple;
a moveable plate;
a bladder that when inflated, forces the movable plate against the staple and out of the housing against the anvil.

15. A method of performing a fundoplication, comprising the steps of:
inserting a device having first and second elongated members into a patient's stomach,
contacting a first portion of the stomach with the first elongated member;
contacting a fundus portion of the stomach with the second elongated member;
moving the distal end of the second elongated member to a position adjacent to the distal end of the first elongated member, thereby moving the fundus portion of the stomach around the esophagus and positioning the fundus portion of the stomach adjacent to the first portion of the stomach; and
fastening the fundus portion that is moved around the esophagus to the first portion of the stomach.

16. The method of claim 15, wherein the fundus portion is wrapped approximately 180 to 360 degrees around the esophagus.

17. The method of claim 15, wherein the fundus portion is wrapped approximately 250 to 290 degrees around the esophagus.

18. The method of claim 15, wherein the fundus portion is wrapped approximately 260 to 280 degrees around the esophagus.

19. The method of claim 15, wherein the fastening step is performed with a staple.

20. The method of claim 15, wherein the contacting steps include the first and the second elongated members moving from a first configuration to a second configuration.

21. The method of claim 20, wherein the second elongated portion includes a distal flexible portion that is expanded on a first plane and a proximal flexible portion that is expanded on a second plane, defining the second configuration.

22. A method of training a person to perform a fundoplication comprising the steps of demonstrating or instructing the method of claim 15.

* * * * *